United States Patent [19]

Hall et al.

[11] Patent Number: 5,567,840
[45] Date of Patent: Oct. 22, 1996

[54] SUBSTITUTED AMINOALKYLPHOSPHINIC ACIDS

[75] Inventors: Roger G. Hall, Manchester, England; Ludwig Maier, Arlesheim; Wolfgang Frostl, Basle, both of Switzerland

[73] Assignee: Ciba-Geigy Corporation, Tarrytown, N.Y.

[21] Appl. No.: 461,090

[22] Filed: Jun. 5, 1995

Related U.S. Application Data

[62] Division of Ser. No. 147,799, Nov. 4, 1993, Pat. No. 5,461,040, which is a division of Ser. No. 873,488, Apr. 22, 1992, Pat. No. 5,281,747, which is a continuation of Ser. No. 725,956, Jun. 27, 1993, abandoned, which is a continuation of Ser. No. 519,707, May 7, 1990, abandoned.

[30] Foreign Application Priority Data

May 13, 1989 [GB] United Kingdom .................. 8911017

[51] Int. Cl.$^6$ ........................................................ C07F 9/30
[52] U.S. Cl. ..................................................... 562/11
[58] Field of Search .................................................. 562/11

[56] References Cited

U.S. PATENT DOCUMENTS

| | | | |
|---|---|---|---|
| 2,535,175 | 12/1950 | Tawney | 260/461 |
| 3,184,496 | 5/1965 | Baranauckas et al. | 260/461 |
| 3,374,288 | 3/1968 | Lange | 260/857 |
| 3,385,822 | 5/1968 | Brown | 260/46.5 |
| 3,493,693 | 2/1970 | Balini | 179/100.2 |
| 3,637,763 | 1/1972 | Firestone | 260/348 |
| 3,784,590 | 1/1974 | Firestone | 260/944 |
| 3,812,221 | 5/1974 | Braden et al. | 260/968 |
| 3,970,586 | 7/1976 | Schliebs et al. | 252/355 |
| 4,064,163 | 12/1977 | Drach et al. | 260/502.4 |
| 4,322,375 | 3/1982 | Maier et al. | 260/951 |
| 4,339,443 | 7/1982 | Baillie et al. | 424/200 |
| 4,390,690 | 6/1983 | Di Giacoma et al. | 528/395 |
| 4,399,287 | 8/1983 | Bailue et al. | 548/119 |
| 4,466,913 | 8/1984 | Tsuruoka et al. | 260/112.5 R |
| 4,469,643 | 9/1984 | Tsuruoka et al. | 260/502.5 G |
| 4,536,355 | 8/1985 | Lee et al. | 260/944 |
| 4,618,358 | 10/1986 | Maier | 71/86 |
| 4,656,298 | 4/1987 | Dingwall et al. | 556/12 |
| 4,657,899 | 4/1987 | Rzeszotarski et al. | 514/120 |
| 4,740,332 | 4/1988 | Thottathil | 260/502.4 R |
| 4,772,738 | 9/1988 | Dingwall et al. | 558/175 |
| 4,908,465 | 3/1990 | Dingwall et al. | 558/175 |
| 5,004,826 | 4/1991 | Dingwall et al. | 558/169 |
| 5,013,863 | 5/1991 | Baylis et al. | 562/11 |
| 5,051,524 | 9/1991 | Baylis et al. | 558/145 |
| 5,190,933 | 3/1993 | Baylis et al. | 514/114 |
| 5,190,934 | 3/1993 | Mickel et al. | 514/114 |
| 5,229,379 | 7/1993 | Marescaux et al. | 514/114 |

FOREIGN PATENT DOCUMENTS

| | | |
|---|---|---|
| 0181833 | 5/1986 | European Pat. Off. |
| 0319479 | 6/1989 | European Pat. Off. |
| 0356128 | 2/1990 | European Pat. Off. |
| 166693 | 12/1964 | U.S.S.R. |
| 1351503 | 5/1974 | United Kingdom |

OTHER PUBLICATIONS

Seabrook et al "Electrophysiological characterization of patent agonists and antagonists at pre-and postsynaptic Gara receptors an neurones in rat brain slices" Br. J. of Pharmacol (1990) vol. 101–909–957.

Lloyd et al "Upregulation of y–Amino–butyric Acid (Gaba) B Binding Sites in Rat Frontal Cortex: A Common Action of Repeated Administration of Different Classes of Antidepressants and Electroshock", The Journal of Pharmacology and Experimental Ther. vol. 23, No. 1 (1986) pp. 72–75.

Rupp et al "Herbicidal methylphosphiaic acid derivatives" Chemical Abstracts vol. 97, (1982)—72585v.

Dingwall et al "New Carboxyphosphonic and phosphinic acid structures of Technical and Biological Interest", Phosphorus and Sulfur (1983) vol. 18 pp. 353–356.

Kreutzkamp et al "Carbonyl and cyanophosphenic acid esters v. conversion of cyano and carboxylic acid ester groups to substituted phosphonic acid esters", Chemical Abstracts, 57., 5946 (1962).

Cates et al "Phosphorus Analogues of y—Aminobutyric Acid, a New Class of Anticonvulsants" J. Med. Chem. vol. 27, pp. 654–659 (1984).

Galllagher et al "Organophosphorus Intermediates V1 The Acid–Catalysed Reaction of Trialkyl Ortho–formates with Phosphinic Acid" Aus. J. Chem. vol. 33 pp. 287–94 (1980).

Hosford et al "The Lethargic Mouse: A Genetic Model of Absence Epilepsy Annual Meetings of the Society for Neuroscience", New Orleans Nov. 10–15 (1991).

Lui et al "Gaba Mediated Mechanism in Experimental Absence Seizures" Neurology 41(Suppl) 151, Abs 131s (1991).

Chem Abstract 76, 72656 K (1972).

*Primary Examiner*—Gary Geist
*Assistant Examiner*—Barbara S. Frazier
*Attorney, Agent, or Firm*—Marla J. Mathias; Henry P. Nowak

[57] ABSTRACT

P-substituted aminoalkylphosphinic acids of the formula $$\underset{R}{\overset{HO}{\diagdown}}\underset{\|}{\overset{O}{P}}-\underset{R_1}{\overset{R_2}{\overset{|}{C}}}-\underset{}{\overset{R_3}{\overset{|}{C}}}-NH_2 \quad (I)$$

wherein R denotes an optionally fluorinated methyl group, $R_1$ denotes hydrogen, lower alkyl, lower alkoxy, hydroxy, halogen or a fluorinated methyl group and $R_2$ and $R_3$ denote hydrogen or $R_2$ denotes hydroxy, lower alkoxy or halogen and $R_3$ is hydrogen or $R_2$ and $R_3$ together represent an oxo group, and their pharmaceutically acceptable salts are active as $GABA_B$-agonists and can be used in the treatment of spinal spasticity, multiple sclerosis and cerebral palsy, trigeminus neuralgia, drug withdrawal syndromes and/or conditions of pain. They can be manufactured by methods known per se and suitable such methods are described.

17 Claims, No Drawings

SUBSTITUTED AMINOALKYLPHOSPHINIC ACIDS

This is a division of Ser. No. 08/147,799, filed Nov. 4, 1993, U.S. Pat. No. 5,461,040, which is a division of Ser. No. 07/873,488, filed Apr. 22, 1992, U.S. Pat. No. 5,281, 747, which is a continuation of Ser. No. 07/725,956, filed Jun. 27, 1991, abandoned, which is a continuation of Ser. No. 07/519,707, filed May 7, 1990, abandoned.

The invention relates to P-substituted aminoalkylphosphinic acids of the formula

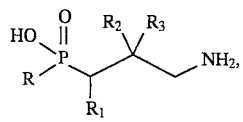

wherein R denotes an optionally fluorinated methyl group, $R_1$ denotes hydrogen, lower alkyl, lower alkoxy, hydroxy, halogen or a fluorinated methyl group and $R_2$ and $R_3$ denote hydrogen or $R_2$ denotes hydroxy, lower alkoxy or halogen and $R_3$ is hydrogen or $R_2$ and $R_3$ together represent an oxo group, and to their pharmaceutically acceptable salts for use in a method for the treatment of the human or animal body, to such methods of treatment, to the use of compounds of the formula I and of their pharmaceutically acceptable salts as medicaments or for the manufacture thereof, to pharmaceutical compositions containing the same and to compounds of the formula I per se with the exception of P-(3-amino-2-oxo-propyl)-P-methyl-phosphinic acid and racemic P-(3-amino-2-hydroxy-propyl)-P-methyl-phosphinic acid, and to their salts with the exception of alkali metal salts and the ammonium salt of P-(3-aminopropyl)-P-methyl-phosphinic acid as well as to a process for the manufacture thereof.

Fluorinated methyl denotes fluoro-, difluoro- or trifluoromethyl.

Within the scope of the invention, there are to be understood by "lower" radicals and compounds, for example, those having up to and including 7, especially up to and including 4, carbon atoms. Also, the general terms have the following meanings:

Lower alkyl is, for example, $C_1$–$C_4$alkyl, such as methyl, ethyl, n-propyl or n-butyl, also isopropyl, isobutyl, secondary butyl or tertiary butyl, but may also be a $C_5$–$C_7$alkyl group, that is to say a pentyl, hexyl or heptyl group.

Lower alkoxy is, for example, $C_1$–$C_4$alkoxy, such as methoxy, ethoxy, n-propoxy or n-butoxy, also isopropoxy, isobutoxy, secondary butoxy or tertiary butoxy, but may also be a $C_5$–$C_7$alkoxy group, that is to say a pentoxy, hexoxy or heptoxy group.

Halogen is, for example, halogen of an atomic number up to and including 35, such as fluorine, chlorine or, less preferred, bromine.

The compounds of the formula I are of amphoteric nature and may be present in the form of internal salts. They also can form acid addition salts and salts with bases. Such salts are particularly pharmaceutically acceptable acid addition salts thereof, as well as pharmaceutically acceptable salts formed with bases. Suitable acids for the formation of acid addition salts are, for example, mineral acids such as hydrochloric, hydrobromic, sulphuric or phosphoric acid, or organic acids such as sulphonic acids, e.g. benzenesulphonic, p-toluenesulphonic or methanesulphonic acid, or carboxylic acids e.g. acetic, lactic, palmitic, stearic, malic, maleic, fumaric, tartaric, ascorbic or citric acid. Salts of compounds of the formula I with bases are, for example, alkali metal salts, e.g. sodium or potassium salts, or alkaline earth metal salts, e.g. calcium or magnesium salts, as well as ammonium salts, such as those with ammonia or organic amines, e.g. diethylamine, di-(2-hydroxyethyl)amine or tri-(2-hydroxyethyl)amine.

Depending on the presence of asymmetric carbon atoms, the compounds of formula I may be in the form of mixtures of isomers, particularly racemates, or in the form of pure isomers, especially optical antipodes.

The compounds disclaimed hereinbefore are known per se. They are, however, novel as pharmaceutical agents. More specifically, while P-(3-aminopropyl)-P-methyl-phosphinic acid is novel per se, the sodium salt thereof has been described in DE-OLS 2032712 [Chem. Abstracts 76, 66,72656 k (1972)]. In this reference, however, the utility ascribed to the sodium and ammonium salts of P-(3-aminopropyl)-P-methyl-phosphinic acid is that of an intermediate for the manufacture of flame retardants or surfactants. There is no suggestion in DE-OLS 2032712 that P-(3-aminopropyl)-P-methyl-phosphinic acid or the salts thereof might have any pharmaceutical activity. P-(3-amino-2-hydroxypropyl)-P-methylphosphinic acid has been described, in its racemate form, in an article by J. G. Dingwall, "Phosphorus and Sulphur", Vol. 18, pages 353–356 (1983). No direct utility is ascribed to this compound in the Dingwall article. P-(3-amino-2-oxo-propyl)-P-methyl-phosphinic acid is described in an article by Natchev, Tetrahedron, Vol. 44/20, pages 6455–6463, (1988). P-(3-amino-2-oxo-propyl)-P-methyl-phosphinic acid is said by Natchev to possess herbicidal activity.

P-(3-Aminopropyl)-P-methyl-phosphinic acid in its free form and the enantiomers of P-(3-amino-2-hydroxy-propyl)-P-methyl-phosphinic acid are novel and, as such, form part of the present invention.

The compounds of this invention have been found to have very strong affinities towards $GABA_B$ receptor sites, with inhibitory concentrations in the low nanomolar range. Specifically, they are $GABA_B$-agonists of high potency is can be demonstrated in vitro, for example, by their potentiation, in the low nanomolar range, of the stimulation of adenylate cyclase by noradrenaline in slices of rat cerebral cortex. In vivo, the compounds of the invention exhibit, in analogy to the known $GABA_B$-agonist β-(aminomethyl)-p-chlorohydrocinnamic acid (baclofen), muscle-relaxant activities as can be shown in the mouse and in the rat, for example, by means of the rotarod test. rats. They also exhibit analgesic activities as can be shown in the phenyl-p-benzoquinone writhing syndrome of the mouse.

The compounds of the invention can be used as muscle relaxants, especially in spinal spasticity, multiple sclerosis and cerebral palsy, and as antispastics and analgesics in trigeminus neuralgia and in the drug-withdrawal syndrome.

Representative compounds of the invention have been found to be much more potent than baclofen in the rotarod test and to have a much longer duration of action. Thus, the inhibitory dose $ID_{50}$ of P-(3-aminopropyl)-P-methyl-phosphinic acid in the rat has been found to more than 20 times lower following oral application and more than 30 times lower following intraperitoneal application than the $ID_{50}$ of baclofen. Also in the mouse, the $ID_{50}$ of P-(3-aminopropyl)-P-methyl-phospinic acid was more than 9 times lower following oral application and 50 times lower following intraperitoneal application than the $ID_{50}$ of baclofen. The duration of action was found to be about three times longer in both species than that of baclofen. On the other hand, the known $GABA_B$-agonist 3-aminopropylphosphinic acid was inactive in either species up to very high doses.

Representative compounds of the invention have to be found to be much more active than baclofen in the phenylp-benzoquinone writhing syndrome of the mouse, too. For example, P-(3-aminopropyl)-P-methyl-phospinic acid was showed an $ID_{50}$ of 0.02 mg/kg s.c. which is about 100 times lower than the $ID_{50}$ of baclofen (1.86 mg/kg s.c.).

The aforementioned advantageous properties render the compositions of this invention of great value as specific therapeutic agents for mammals including man.

The invention relates in the first place to compounds of the formula I, wherein R denotes methyl, fluoromethyl, difluoromethyl or trifluoromethyl, $R_1$ denotes hydrogen, lower alkyl, lower alkoxy, hydroxy, halogen, fluoromethyl, difluoromethyl or trifluoromethyl and $R_2$ and $R_3$ denote hydrogen or $R_2$ denotes hydroxy, lower alkoxy or halogen and $R_3$ denotes hydrogen or $R_2$ and $R_3$ together represent oxo, and their pharmaceutically acceptable salts for use in a method for the treatment of the human or animal body, to pharmaceutical compositions containing the same and to compounds of the formula I per se with the exception of P-(3-amino-2-oxo-propyl)-P-methyl-phosphinic acid and racemic P-(3-amino-2-hydroxy-propyl)-P-methyl-phosphinic acid, and to their salts with the exception of alkali metal salts and the ammonium salt of P-(3-aminopropyl)-P-methyl-phosphinic acid as well as a process for the manufacture thereof.

The invention relates especially to compounds of the formula I, wherein R denotes methyl, fluoromethyl, difluoromethyl or trifluoromethyl, $R_1$ denotes hydrogen or $C_1$–$C_4$alkyl, such as methyl or ethyl, $R_2$ denotes hydrogen or hydroxy and $R_3$ denotes hydrogen or $R_2$ and $R_3$ together represent oxo, and their pharmaceutically acceptable salts for use in a method for the treatment of the human or animal body, to pharmaceutical compositions containing the same and to compounds of the formula I per se with the exception of P-(3-amino-2-oxo-propyl)-P-methyl-phosphinic acid and racemic P-(3-amino-2-hydroxy-propyl)-P-methyl-phosphinic acid, and to their salts with the exception of alkali metal salts and the ammonium salt of P-(3-aminopropyl)-P-methyl-phosphinic acid as well as to a process for the manufacture thereof.

The invention relates also to compounds of the formula I, wherein R denotes methyl, fluoromethyl, difluoromethyl or trifluoromethyl, $R_1$ denotes hydroxy and $R_2$ and $R_3$ are hydrogen, and to their salts.

The invention relates very especially to compounds of the formula I, wherein R denotes methyl, $R_1$ is hydrogen, and wherein $R_2$ represents hydrogen or hydroxy and $R_3$ is hydrogen or $R_2$ and $R_3$ together represent oxo, with the exception of P-(3-amino-2-oxo-propyl)-P-methyl-phosphinic acid, provided that, when $R_2$ denotes hydroxy, the C-atom it is attached to has S-configuration, in the free form, to pharmaceutical compositions containing them and to a process for the manufacture thereof.

The invention relates specifically to the compounds of the formula I described in the examples, to their manufacture and/or use.

The invention relates very specifically to P-(3-aminopropyl)-P-methyl-phosphinic acid and P-[3-amino-2(S)-hydroxy-propyl]-P-methyl-phosphinic acid in the free form and to pharmaceutical compositions containing the same or P-(3-amino-2-oxo-propyl)-P-methyl-phosphinic acid in the free form.

According to the present invention, there is also provided a process for the manufacture of compounds of formula I, characterised in that a) in a compound of formula

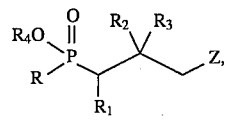

in which R, $R_1$, $R_2$ and $R_3$ have their previous significances, Z is —$NH_2$ and $R_4$ is a hydroxy-protective group $R_5$ or, when R is methyl and $R_1$, $R_2$ and $R_3$ are hydrogen, $R_4$ is an alkali metal or ammonium ion $R_6$, or Z is a protected or latent amino group $Z_0$, and $R_4$ is hydrogen or a hydroxy-protective group $R_5$, and wherein a carbonyl group formed by $R_2$ and $R_3$ together with the carbon atom to which they are attached may also be present in a temporarily protected form, any group $R_5$ or $R_6$ is replaced by hydrogen and/or any group $Z_0$ is converted into —$NH_2$ and/or, if $R_2$ and $R_3$ together with the carbon atom to which they are attached form a protected carbonyl group, such protecting group is removed; or b) in a compound of the formula

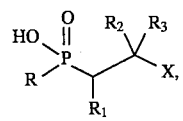

in which R, $R_1$, $R_2$ and $R_3$ have their previous significances and X is a group capable of being converted into the group of formula —$CH_2$—$NH_2$ (Ia), the group X is converted into the group; or c) a compound of formula I' being identical to a corresponding compound of formula I apart from having one or more carbon-carbon multiple bond(s) is reduced to produce a compound of formula I wherein R has its previous significance, $R_1$ is hydrogen, lower alkyl or fluorinated methyl and $R_2$ and $R_3$ are hydrogen, and, if desired, a resulting compound is converted into another compound of the formula I, a resulting mixture of isomers is separated into the individual isomers and/or a resulting salt obtained in this process is converted into the free compound of the formula I or into another salt and/or, if desired, a resulting free compound of the formula I is convened into a salt to correspond to the above definition.

Protected hydroxy groups such as groups —$OR_5$ in starting materials of the formula II are, for example, etherified hydroxy groups, such as hydroxy groups etherified with an aliphatic, cycloaliphatic or araliphatic alcohol, e.g. with a $C_1$–$C_7$alkanol, a $C_1$–$C_7$-alkanoyloxy-$C_1$–$C_7$-alkanol, a cycloalkanol, or a $C_1$–$C_7$-alkanol substituted by one or two optionally substituted phenyl groups, or hydroxy groups etherified with an aliphatic silanol, e.g. with a tri-$C_1$–$C_7$alkylsilanol. As groups $R_5O$—, $C_1$–$C_7$alkoxy, e.g. $C_1$–$C_4$alkoxy, mono- or diphenyl-$C_1$–$C_7$-alkoxy, e.g. 1-phenyl- or 1,1-diphenyl-$C_1$–$C_4$-alkoxy, and tri-lower alkylsilyloxy, e.g. tri-$C_1$–$C_4$-alkyl—, such as trimethylsilyloxy, are especially preferred.

Protected amino groups such as groups $Z_0$ in starting materials of the formula II are, for example, acylamino groups such as $C_1$–$C_7$alkanoylamino, e.g. acetylamino, or phthalimido, $C_1$–$C_7$alkoxycarbonylamino groups unsubstituted or substituted by phenyl, e.g. benzyloxycarbonylamino or tert.-butoxycarbonylamino, or 1-aryl-$C_1$–$C_7$-alkylamino groups, e.g. benzylamino, or silylated amino groups, such as tri-$C_1$–$C_7$-alkylsilylamino or especially bis(tri-$C_1$–$C_7$-alkylsilyl)amino, e.g. bis(trimethylsilyl)amino. A latent amino group $Z_0$ may be e.g. nitro or azido.

Preferred compounds of formula II are those having the formula

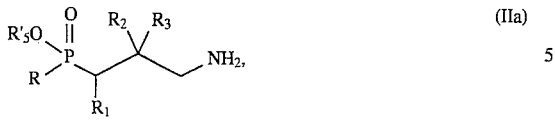
(IIa)

wherein $R'_5$ represents a hydroxy- protective group, for example, $C_1$–$C_4$alkyl or $C_1$–$C_4$-alkyl substituted by $C_1$–$C_7$alkanoyloxy or by one or two optionally substituted phenyl groups, such as 1-($C_2$–$C_7$alkanoyloxy)-$C_1$–$C_4$-alkyl, e.g. pivaloyloxymethyl, or 1-phenyl- or 1,1-diphenyl-$C_1$–$C_4$alkyl, e.g. benzyl, or having the formula

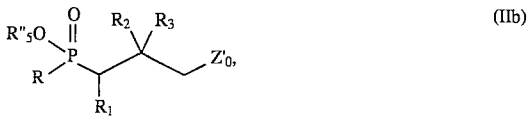
(IIb)

wherein $R''_5$ represents a hydroxy-protective group, for example, $C_1$–$C_4$-alkyl or $C_1$–$C_4$-alkyl substituted by one or two optionally substituted phenyl groups, such as 1-phenyl- or 1,1-diphenyl-$C_1$–$C_4$-alkyl, e.g. benzyl, or a silyl group, such as tri-$C_1$–$C_4$-alkylsilyl, e.g. trimethylsilyl, and $Z'_0$ denotes, for example, $C_1$–$C_7$-alkanoylamino, e.g. acetylamino, phthalimido or bis(silyl)amino, such as bis(tri-$C_1$–$C_4$-alkylsilyl)amino, e.g. bis(trimethylsilyl)amino, or having the formula

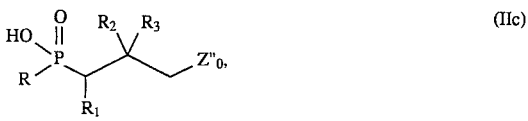
(IIc)

wherein $Z''_0$ denotes, for example, $C_1$–$C_7$-alkanoylamino, e.g. acetylamino, $C_1$–$C_4$alkoxy-carbonylamino, e.g. tert.-butoxycarbonylamino, or phenyl-$C_1$–$C_4$-alkoxy-tert.butoxycarbonylamino, or phenyl-$C_1$–$C_4$-alkoxycarbonylamino, or having the formula

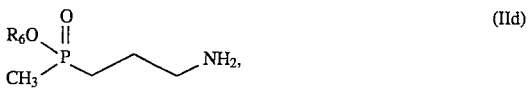
(IId)

wherein $R_6$ denotes an alkali metal or ammonium ion; and wherein in formulae IIa, IIb and IIc R, $R_1$, $R_2$ and $R_3$ have their previous significances.

The replacement of the protective group $R_5$, $R'_5$ or $R''_5$ in compounds of formula II, IIa or IIb by hydrogen may be effected by treatment with a suitable nucleophilic reagent, such as an alkali metal hydroxide, e.g. sodium or lithium hydroxide, an alkali metal halide, particularly bromide or iodide, such as lithium bromide or sodium iodide, thiourea or an alkali metal thiophenolate, such as sodium thiophenolate. The replacement reaction may be carried out in the absence or presence of a solvent and, if necessary, while cooling or heating, in a closed vessel and/or under an atmosphere of an inert gas.

When $R_5$, $R'_5$ or $R''_5$ denotes $C_1$–$C_4$alkyl substituted in 1-position by one or two phenyl groups, benzyl, the replacement of such a group in compounds of formula II, IIa or IIb by hydrogen may be effected by hydrogenolysis in the presence of a metallic hydrogenation catalyst, or any other suitable procedure.

Alternatively, the replacement of the protective group, e.g. of a silyl group $R_5$ or $R'_5$ in compounds of formula II or IIb, of an alkyl group $R_5$, $R'_5$ or $R''_5$ in compounds of formula II, IIa or IIb, or of an alkali metal or ammonium ion $R_6$ in compounds of the formula II or IId by hydrogen may be effected by treatment with an acid under hydrolytic conditions, especially with a mineral acid such as hydrohalic acid, e.g. hydrochloric acid, which is used in diluted or concentrated aqueous form, or by treatment with an organic silyl halide such as trimethylsilyl iodide or bromide, followed by hydrolysis, if necessary. The reaction is preferably conducted at elevated temperature e.g. while refluxing the reaction mixture and, if necessary, using an organic diluent, in a closed vessel and/or under an atmosphere of an inert gas.

Protected amino groups $Z_0$, $Z'_0$ or $Z''_0$ in compounds of formula II, IIb or IIc or latent amino groups $Z_0$ in compounds of formula II may be converted into free amino according to known methods, which are selected according to the characteristics of the protected or latent amino group to be converted into amino, such as solvolytic or hydrogenolytic procedures, for example, hydrolysis in the presence of an acid or a base, acidolysis, e.g. treatment with trifluoroacetic acid, treatment with hydrazine, or hydrogenolysis in the presence of a metallic hydrogenation catalyst, or any other suitable procedure.

Depending on the groups involved, the replacement and conversion operations may be carried out in any sequence or simultaneously by methods which are well known per se.

It is preferred that all protecting groups are converted, $R_5$, $R'_5$, $R''_5$ or $R_6$ being converted to hydrogen, a carbonyl group, formed by $R_2$ and $R_3$ together with the carbon atom to which they are attached, in protected form being converted to a carbonyl group and $Z_0$, $Z'_0$ or $Z''_0$ being convened to —$NH_2$, in a single step, by treatment with an acid, preferably a hydrohalic acid, especially hydrochloric acid, under hydrolytic conditions.

The compounds of formula II may be prepared by various methods, for example according to the nature of the group X' in the formula V defined hereinafter, e.g. by reacting, in the presence of a basic catalyst or in the presence of agents forming free radicals, a compound of the formula

(IV)

in which R and $R_4$ have their previous significances, with a compound of formula

(V)

in which $R'_1$ is hydrogen, lower alkyl or fluorinated methyl, $R'_2$ is hydrogen or lower alkoxy and X' is a group X, which can be convened into the group Ia, or is a group —$CH_2$—$Z_0$ (VIa) in which $Z_0$ has its previous significance, in order to produce a compound of formula

(VI)

wherein R, $R'_1$, $R'_2$, $R_4$ and X' have their previous significances, and which compound VI, when X' is a group VIIa, is identical to a compound II wherein $R_1$ is $R'_1$, $R_2$ is $R'_2$, $R_3$ is hydrogen and Z is $Z_0$; and then, if a compound II is to be prepared wherein Z is amino, $R_1$ is $R'_1$, $R_2$ is $R'_2$ and $R_3$ is hydrogen, converting the group X' which is a group X into the group of formula Ia.

A group X is primarily cyano but may also represent carbamoyl or a group of the formula —CH=Y in which Y is a free or functionally modified oxo group such as a corresponding acetal or thioacetal group, including a corresponding cyclic group.

When, in the compound of formula V, X' is cyano or carbamoyl, then either a basic catalyst or a free radical catalyst may be employed. When, however, in the compounds of formula V, X' is e.g. a residue of formula —CH$_2$—Z$_0$ or —CH=Y, then a free radical catalyst is required.

A basic catalyst used in the first step may be e.g. an alkali metal C$_1$–C$_4$alkoxide, for example, a sodium or potassium C$_1$–C$_4$alkoxide, in particular sodium methoxide, sodium ethoxide or potassium tert.-butoxide, an alkali metal or alkaline earth metal fluoride such as potassium fluoride or caesium fluoride, or an alkali metal hydride, such as sodium hydride.

The reaction may be effected with or without the use of an added solvent. If a solvent is added, this is preferably an alcohol, in particular a C$_1$–C$_4$alkanol corresponding to the alkoxide used as basic catalyst. The reaction temperature may vary from 0° C. to the boiling point of any added solvent.

Agents forming free radicals are, for example, compounds convertible into free radicals by ionising or ultra-violet radiation, preferably peroxy compounds, such as inorganic peroxy compounds, e.g. hydrogen peroxide or ammonium persulphate, or organic peroxides, e.g. benzoyl peroxide or tert.-butyl peroxide, or organic azo compounds, e.g. azo-bis-isobutyronitrile. Reactions involving free radical-forming agents may be conducted in the optional presence of a solvent and, if necessary, while cooling or heating, in a closed vessel and/or in an atmosphere of an inert gas.

The conversion of a group X into the group Ia is carried out according to known methods. Cyano and carbamoyl are converted into aminomethyl by reduction, cyano, for example, by hydrogenation in the presence of a suitable catalyst, e.g. Raney nickel, and of a solvent, such as ethanol, which may preferably contain ammonia, and carbamoyl, for example, by treatment with a suitable hydride reducing agent, such as borane in tetrahydrofuran. The conversion of a group —CH=Y into a group Ia is carried out by known deprotection followed by reductive amination procedures, e.g. treatment with sodium cyanoborohydride in the presence of ammonium acetate in a suitable solvent, such as dioxane, and while cooling, e.g. at about 0° C.

The compounds of formula IV are either known or they may be prepared e.g. by reaction of a compound of the formula R—P(Hal)$_2$ (IVa; Hal=halogen) with an alcohol R$_4$OH in the presence of a tri-C$_1$–C$_7$-alkylamine. Specific examples of compounds of formula IV include: isopropyl (methyl)phosphonite and isobutyl (methyl)phosphonite.

Likewise, compounds of formula V are either known or can be obtained by methods which are well known.

Alternatively, in order to produce a compound of formula II wherein R$_4$ is C$_1$–C$_4$-alkyl or C$_1$–C$_4$-alkyl substituted by one or two optionally substituted phenyl groups and R$_1$ is R'$_1$, a compound of the formula

(VII)

in which R has the meaning indicated, R'''$_5$ is C$_1$–C$_4$alkyl or C$_1$–C$_4$alkyl substituted by one or two optionally substituted phenyl residues and each R$_7$, independently, is C$_1$–C$_7$alkyl, preferably C$_1$–C$_4$alkyl, particularly methyl, the groups R'''$_5$ and R$_7$ being the same or different, can be reacted with a compound of the formulae

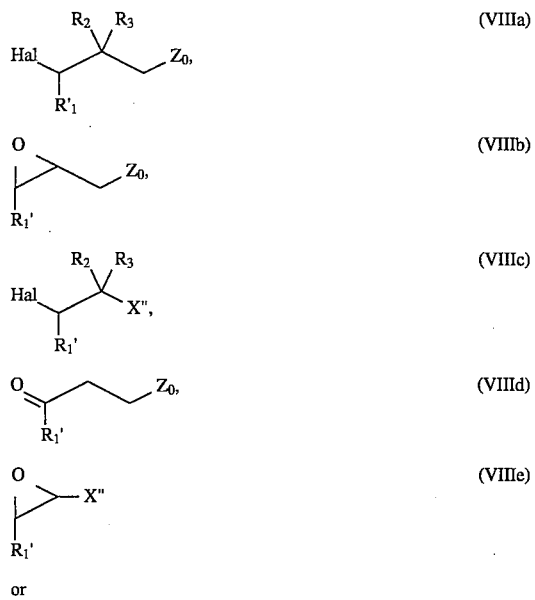

or in which R$_2$, R$_3$ and Z$_0$ have their previous significances, hydroxy R$_2$ or oxo R$_2$+R$_3$ being present in a temporarily protected form, R$_1$' is hydrogen, lower alkyl or a fluorinated methyl group, X" is primarily cyano or a group of the formula —CH=Y in which Y has its previous significance, which groups are subsequently converted into the group Ia, and Hal stands for halogen, such as iodo, bromo or chloro.

The reaction with an epoxide of formulae VIIIb or VIIIe is advantageously carried out in the presence of a mild Lewis acid, such as anhydrous zinc chloride, whilst the reaction with a halide of formula VIIIa or VIIIc is preferably carried out under the conditions of the Arbusov method, e.g. at a reaction temperature ranging from room temperature to 200° C., e.g. to 160° C., while removing the trialkyl silyl halide formed in the reaction.

In a modification of the reaction between a compound of formula VII and a compound of formula VIIIb, a compound of formula II wherein R$_1$ is R'$_1$, R$_2$ is hydroxy, R$_3$ is hydrogen, R$_4$ is R'''$_5$ and Z is Z$_0$ may be produced by reacting a compound of formula VII with a compound of formula

(VIIIf)

in which R$_1$' is hydrogen, lower alkyl or a fluorinated methyl group and Y$_1$ is a leaving group, for example, a reactive esterified hydroxy group, e.g. an arylsulphonyloxy group such as a tosyl group, and in which compound of formula VIIIf may be in racemic form or in the form of a single optically active isomer, to produce a compound of formula

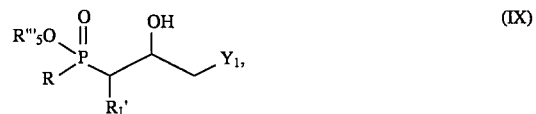

(IX)

in which R, R'$_1$ R'''$_5$ and Y$_1$ have their previous significances, and converting Y$_1$ into a group Z$_0$, e.g. by reaction with sodium azide.

Compounds of formula II may also be prepared starting from and N-protecting a compound of formula

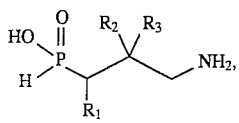   (X)

wherein $R_1$, $R_2$ and $R_3$ have their previous significances, to give a compound of formula

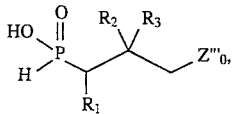   (XI)

wherein $R_1$, $R_2$ and $R_3$ have their previous significances and $Z'''_0$ is $Z'_0$ or $Z''_0$, and, subsequently, protecting also the (acid) hydroxyl group in the compound of formula XI to produce a compound of formula

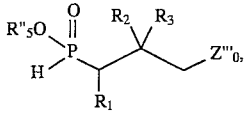   (XII)

wherein $R_1$, $R_2$, $R_3$, $R''_5$ and $Z'''_0$ have their previous significances.

Alternatively, in a preferred embodiment of process variant a), the starting material of formula X can be reacted with a silylating agent, such as a hexa-$C_1$–$C_7$-alkyldisilazane or a tri-$C_1$–$C_7$-alkyl halogenosilane, e.g. with hexamethyldisilazane or trimethylchlorosilane, in the presence of triethylamine, to produce a compound of formula

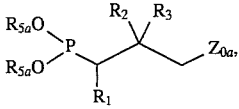   (XII')

wherein $R_1$, $R_2$ and $R_3$ have their previous significances, $R_{5a}$ denotes tri-$C_1$–$C_7$-alkylsilyl, e.g. trimethylsilyl, and $Z_{0a}$ denotes tri-$C_1$–$C_7$-alkylsilylamino, such as trimethylsilylamino.

The intermediate of the formula XII or XII' is then reacted with a compound capable of converting the

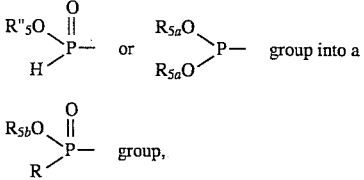

wherein R has its previous significance and $R_{5b}$ is $R''_5$ or $R_{5a}$, to produce the corresponding compound of formula II, in which $R_4$ is $R_{5b}$ and Z is $Z_{0a}$ or $Z'''_0$. Thus, the intermediate XII or XII' may be reacted with a compound of the formula R—$Y_2$ (XII''), wherein $Y_2$ is a reactive esterified hydroxyl group, e.g. a halogen atom or a sulphonyloxy group such as p-toluenesulphonyloxy, for example, with methyliodide, fluoromethyl iodide, difluoromethyl iodide or trifluoromethyl iodide.

Most starting materials of formula X and their production have been described in U.S. Pat. No. 4,656,298. Novel compounds of the formula X can be prepared in an analogous manner.

In another preferred embodiment of process variant a), a compound of the formula

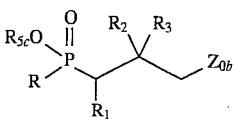   (IIb')

wherein R, $R_1$, $R_2$ and $R_3$ have their previous significances, $R_{5c}$ is tri-$C_1$–$C_7$-alkylsilyl and $Z_{0b}$ is $Z_{0a}$ or $Z'''_0$ which compound IIb' may be prepared, for example, in a manner analogous to that shown in the reaction sequence

X→XI→XII→IIb' or
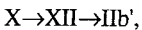
X→XII→IIb', is subjected to basic or acidic hydrolysis to produce the corresponding compound II, wherein $R_4$ is hydrogen and Z is $Z_{0b}$. Advantageously, a compound IIb', wherein $R_{5c}$ denotes tri-$C_1$–$C_7$-alkylsilyl, $Z_{0b}$ denotes tri-($C_1$–$C_7$-alkylsilyl)amino and R, $R_1$, $R_2$ and $R_3$ have their previous significances, is formed in situ by reacting a compound of the formula X with a silylating agent and subsequently, preferably under basic conditions, with a compound XII'' and deprotected according to the invention, when worked up under protic, e.g. aqueous/alcoholic conditions.

Compounds of the formula II, wherein $R_2$ denotes hydroxy and $R_3$ represents hydrogen or $R_2$ and $R_3$ together denote oxo, may be produced by reacting a compound having the formula

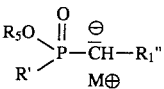   (XIII)

in the form of the salt of the formula

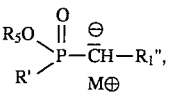   (XIII')

wherein $R_5$ has its previous significance, either R' is optionally fluorinated methyl and $R_1''$ is hydrogen or fluorinated methyl, or R' is trifluoromethyl and $R_1''$ is lower alkyl, and M is an alkali metal, alkaline earth metal or transition metal, preferably lithium, sodium or potassium, calcium, zinc or tin, with a compound having the formula

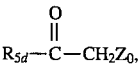   (XIV)

wherein $R_{5d}$ denotes etherified hydroxy such as specified for $R_5$, halogeno, such as chloro or bromo, or hydrogen and $Z_0$ has its previous significance, to produce a compound having the formula II wherein $R_4$ is $R_5$, R is R', Z is $Z_0$, $R_1$ is $R'_1$, $R_2$ is hydroxy and $R_3$ denotes hydrogen or $R_2$ and $R_3$ together denote oxo.

The conversion of the group X into a group of formula —$CH_2$—$NH_2$ according to process variant b) may be effected by any of the methods described hereinbefore, e.g. by a variation of the conversion of compounds of formula VI into compounds of formula II. The reaction is carried out according to known methods, in the absence or presence of a solvent, which may also serve as a reagent, if necessary, while cooling or heating, in a closed vessel and/or in the atmosphere of an inert gas.

The starting material of the formula III may be prepared, for example, from compounds of a type similar to those of the formula VI, wherein $R_4$ is a group $R_5$ having its previous significance, by converting the group $R_5O$— into hydroxy, the reaction being carried out according to the previously described procedure, e.g. by acidic hydrolysis, such as by treatment with an aqueous mineral acid, e.g. hydrochloric acid, or by treatment with a nucleophilic reagent.

In process variant c), a compound of formula I' may have its unsaturation 1) within a substituent $R''_1$ corresponding after the reduction to the substituent $R_1$ in the end product of the formula I; or 2) between the carbon atom carrying the substituent $R_1$ and the carbon atom carrying the substituents $R_2$ and $R_3$ in the end product of the formula I. In the former case, the compound of formula I' will have the formula

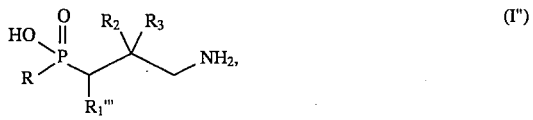

in which R, $R_2$ and $R_3$ have their previous significances and $R_1'''$ is $C_2$–$C_7$-alkenyl or $C_2$–$C_7$-alkynyl. In the latter case, the compound of the formula I' will have the formula

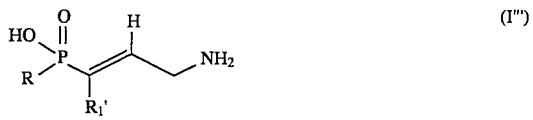

wherein R has its previous significance and $R_1'$ is hydrogen, lower alkyl or a fluorinated methyl group.

The reduction may be effected by any suitable reducing agent, such as hydrogen in the presence of a catalyst for the reduction of aliphatic multiple bonds e.g. palladium on charcoal, in the presence or absence of a solvent and at room temperature or elevated temperature.

The unsaturated compounds of formula I' may be produced according to any of the methods described herein for the manufacture of compounds of formula I, starting from corresponding unsaturated starting materials. The above-mentioned reactions are carried out according to standard methods, in the presence or absence of diluents, preferably such as are inert to the reagents and are solvents therefore, of catalysts, condensing or said other agents, respectively, and/or of inert atmospheres, at low temperatures, room temperature or elevated temperatures, preferably near the boiling point of the solvents used, and at atmospheric or super-atmospheric pressure.

Compounds of the formula I obtainable according to the process of the invention may be interconverted into one another.

Thus, compounds of formula I, wherein $R_1$ and/or $R_2$ denotes hydroxy, can be converted into the corresponding hydroxy-free compounds, for example, by reacting with thiocarbonyldiimidazole and treating the resulting imidazolylthiourethane in the presence of a radical-initiator, such as azo-bis-isobutyronitrile, with a tri-$C_1$–$C_7$alkylstannane, e.g. with $(C_4H_9)_3SnH$, for example in benzene at 60° to 80° C.

Compounds of formula I, wherein $R_2$ and $R_3$, together with the carbon atom to which they are both attached, form a carbonyl group, may be converted into compounds in which $R_2$ is hydroxy and $R_3$ is hydrogen, by known reductive methods and vice versa, compounds of the formula I, wherein $R_2$ is hydroxy and $R_3$ is hydrogen, may be converted by known oxidative methods into the corresponding compounds I, wherein $R_2+R_3$ are oxo.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts and/or racemates or optically pure antipodes.

Whenever desirable, the above processes are carried out after first suitably protecting any potentially interfering reactive functional groups, e.g. as illustrated herein. Advantageously, those starting materials should be used in the reactions described hereinbefore that lead to the formation of those compounds indicated above as being preferred. The invention relates also to novel starting materials and processes for their manufacture.

Depending on the choice of starting materials and methods, the new compounds may be in the form of one of the possible isomers, for example, as diastereomers, as optical isomers (antipodes), as racemates, or as mixtures thereof. If diastereomeric mixtures of the above compounds or intermediates are obtained, these can be separated into the single racemic or optically active isomers by methods in themselves known, e.g. by fractional distillation, crystallisation or chromatography. The racemic products of formula I or basic intermediates can be resolved into the optical antipodes, for example, by separation of diastereomeric salts thereof, e.g. by the fractional crystallisation of their (D)- or (L)-(tartrate, dibenzoyltartrate, mandelate or camphorsulphonate) salts. Advantageously, the more active of the antipodes of the compounds of this invention is isolated.

Furthermore, the compounds of the invention are either obtained in the free form, i.e. in the form of an internal salt ("Zwitterion" form), or as acid addition salts or salts with bases. For example, any resulting free compound can be convened into a corresponding acid addition salt, preferably with the use of a pharmaceutically acceptable acid or anion exchange preparation, or into a salt with bases by treatment of the free compounds with bases or suitable cation exchange techniques, or resulting salts can be converted into the corresponding free compounds, for example the acid addition salts, with the use of a stronger base, such as a metal or ammonium hydroxide, or any basic salt, e.g., an alkali metal hydroxide or carbonate, or a cation exchange preparation and the salts with bases by treatment with suitable acidic reagents.

These or other salts, for example the picrates, can also be used for purification of the compounds obtained; the compounds are then first converted into salts. In view of the close relationship between the free compounds and the compounds in the form of their salts, whenever a compound is referred to in this context, a corresponding salt is also intended, provided such is possible or appropriate under the circumstances and the term "salts" shall, if desired also include the free compounds, where appropriate according to meaning and purpose. The compounds, including their salts, may also be obtained in the form of their hydrates, or include other solvents used for the crystallisation.

The pharmaceutical compositions according to the invention which contain compounds of the formula I or pharmaceutically acceptable salts thereof, are intended for enteral, such as oral or rectal, as well as parenteral administration and contain the pharmacologically active ingredient alone or in admixture to customary pharmaceutically acceptable carriers.

The pharmaceutical compositions of the invention contain, for example, from approximately 10% to 80%, preferably from approximately 20% to 60%, of the active ingredient. Pharmaceutical compositions according to the invention intended for enteral and parenteral administration are, for example, pharmaceutical compositions in dose unit form, such as dragées, tablets, capsules or suppositories, and also ampoules for injection. They are manufactured in a manner known per se, by means of conventional mixing, granulating, confectioning, dissolving or lyophilisating processes. For example, pharmaceutical compositions for oral administration can be obtained by combining the active ingredient with solid carriers, if desired granulating the resulting mixture and processing the mixture or granulate obtained, if desired or necessary after addition of suitable adjuncts, into tablets, tablet cores, dragées or capsules.

The present invention also relates to the use of the compounds of the invention for the preparation of pharmaceutical compositions, especially pharmaceutical compositions having selective $GABA_B$ agonistic activity which can be used in the treatment of spinal spasticity, multiple sclerosis, cerebral palsy, trigeminus neuralgia, drug withdrawal syndromes and/or conditions of pain.

These preparations may be used especially in the above-mentioned indications, if they are administered orally or parenterally, such as intravenously, intramuscularly or subcutaneously. The necessary dose depends on the particular disorder to be treated, its severity and the duration of therapy. The number and quantity of the individual doses and also the administration scheme is best determined on the basis of an individual examination of the host concerned, these methods being known to those skilled in the art. As a rule, however, a therapeutically active quantity of a compound of this invention is in the dosage range of about 0.1 to 10 mg/kg body weight per day. The pharmaceutical preparations are manufactured according to known methods, using standard auxiliary substances.

The following Examples further illustrate the present invention. Temperatures are given in degrees centigrade; pressures in mbar.

EXAMPLE 1

A solution of 10.0 g of isobutyl P-(3-aminopropyl)-P-methyl-phosphinate in 60 ml of 36% aqueous hydrochloric acid is heated to reflux for a period of 15 hours. The reaction mixture is then allowed to cool to room temperature, concentrated under reduced pressure, and co-evaporated twice with 50 ml of water. The crude material is dissolved in water, washed with ether and the aqueous layer evaporated to dryness. The crude product is dissolved in 50 ml of methanol, 1–2 ml of propylene oxide are added and the mixture is stirred until the precipitated solid is free of halogen. The solid is filtered and dried to give P-(3-aminopropyl)-P-methyl-phospinic acid, m.p. 270°–278°, $^{31}$P-NMR spectrum: δ=+42.1 ppm ($D_2O$).

The starting material may be prepared as follows:

A solution of 15.0 g of isobutyl P-methylphosphonite and 5.3 g of acrylonitrile in 50 ml of dry ethanol is added to a stirred mixture of 0.5 g of sodium (50% dispersion in oil) in 25 ml of ethanol, at 0° C., under an atmosphere of nitrogen. The reaction mixture is allowed to warm to room temperature, and stirred for 4 hours. 1 ml of glacial acetic acid is added and the mixture is concentrated under reduced pressure. The resulting crude product is dissolved in 50 ml of ethyl acetate, washed twice with 20 ml of water, and the organic extract is dried over magnesium sulphate, and then concentrated under reduced pressure. The crude product is distilled to give isobutyl P-(2-cyanoethyl)-P-methyl-phosphinate, b.p. 140°/0.2 mbar, $^{31}$P-NMR spectrum: δ=+50.5 ppm ($CDCl_3$).

A solution of 20.0 g of isobutyl P-(2-cyanoethyl)-P-methyl-phosphinate in 200 ml of ethanol is added to 230.0 g of an 8% solution of ammonia in ethanol. To this are added 15 ml of Raney nickel slurry and the resulting mixture is hydrogenated at 1 bar until hydrogen uptake ceases. The mixture is then filtered and the filtrate is concentrated under reduced pressure. The crude product is distilled under reduced pressure to give isobutyl P-(3-aminopropyl)-P-methyl-phosphinate, b.p. 130°/0.01 mbar, $^{31}$P-NMR spectrum: δ=+57.6 ppm ($CDCl_3$).

EXAMPLE 2

A solution of 21.5 g of isobutyl P-(4-aminobut-2-yl)-P-methyl-phosphinate in 80 ml of 36% aqueous hydrochloric acid is heated to reflux for a period of 10 hours. The reaction mixture is then allowed to cool to room temperature, concentrated under reduced pressure, and co-evaporated twice with 100 ml of water. The crude material is dissolved in water, washed with chloroform, and the aqueous layer treated with activated charcoal. The aqueous solution is filtered hot, evaporated to dryness, the crude product is dissolved in 50 ml of methanol and treated with 1–2 ml of propylene oxide. The hygroscopic solid is filtered and triturated with acetone. After drying, P-(4-aminobut-2-yl)-P-methyl-phosphinic acid is obtained as a hygroscopic solid, m.p. 68°–75°, $^3$P-NMR spectrum: δ=+46.5 ppm ($D_2O$).

The starting material may be prepared as follows:

A solution of 50.0 g of isobutyl P-methylphosphonite and 22.8 g of crotononitrile in 50 ml of dry ethanol is added to a stirred mixture of 0.8 g of sodium hydride (50% dispersion in oil) in 25 ml of ethanol at 0° C., under an atmosphere of nitrogen. The reaction mixture is allowed to warm to room temperature and stirred for 4 hours. 1 ml of glacial acetic acid is added and the mixture is concentrated under reduced pressure. The resulting crude product is dissolved in 50 ml of ethyl acetate, washed twice with 25 ml of water, and the organic extract is dried over magnesium sulphate, and then concentrated under reduced pressure. The crude product is distilled to give isobutyl P-(3-cyanoprop-2-yl)-P-(methyl)-phosphinate, b.p. 110°/0.125 mbar, $^{31}$P-NMR spectrum: δ=+55.9 and +55.5 ppm ($CDCl_3$).

A solution of 29.8 g of isobutyl P-(3-cyanoprop-2-yl)-P-methyl-phosphinate in 200 ml of ethanol is added to 310.0 g of an 8% solution of ammonia in ethanol. To this are added 20 ml of Raney nickel slurry, and the resulting mixture is hydrogenated at 1 bar until hydrogen uptake ceases. The mixture is then filtered and the filtrate is concentrated under reduced pressure. The crude product is distilled under reduced pressure to give isobutyl P-(4-aminobut-2-yl)-P-methyl-phosphinate, b.p. 100°/0.1 mbar, $^{31}$P-NMR spectrum: δ=+58.9 and +58.4 ppm ($CDCl_3$).

EXAMPLE 3

A solution of 9.6 g isobutyl P-(2-hydroxy-3-phthalimido-propyl)-P-methylphosphinate in 100 ml of 36% aqueous hydrochloric acid is heated to reflux for a period of 15 hours. The reaction mixture is then allowed to cool to room temperature, concentrated under reduced pressure, and co-evaporated three times with 25 ml of water. The crude material is dissolved in 50 ml of water, washed with 20 ml of ether and the aqueous layer is treated with activated charcoal. The aqueous solution is filtered hot, the filtrate evaporated to dryness and the crude product dissolved in 50 ml of ethanol. 1–2 ml of propylene oxide are added and the solution stirred until the precipitate is free of halogen. Filtration and drying then gives P-(3-amino-2-hydroxy-propyl)-P-(methyl)-phosphinic acid, m.p. 207°–208°; $^{31}$P-NMR spectrum: δ=38.9 ppm ($D_2O$).

The starting material may be prepared as follows:

To a solution of 12.1 g of isobutyl O-trimethylsilyl-P-methyl-phosphonite in 100 ml of dry tetrahydrofuran are added 11.8 g of 2,3-epoxypropylphthalimide followed by 0.5 g of dry zinc chloride. The mixture is heated to reflux for a period of 2 hours under an inert gas atmosphere. The mixture is allowed to cool to room temperature, the solvent is evaporated under reduced pressure, the residue dissolved in 100 ml of chloroform, and this is stirred vigorously with 50 ml of water for a period of 0.5 hours. The organic layer is separated, dried over magnesium sulphate and the solvent is removed under reduced pressure. The residue is triturated with 50 ml of hexane:ether 1:1, and the resulting white solid filtered and dried to give isobutyl P-(2-hydroxy-3 -phthalimido-propyl)-P-methyl-phosphinate, m.p. 110°–113°; $^{31}$P-NMR spectrum: $\delta$=+54.8 and +53.5 ppm (CDCl$_3$).

EXAMPLE 4

A solution of 1.1 g of isobutyl P-[3-amino-2(S)-hydroxy-propyl]-P-methyl-phosphinate in 20 ml of 36% aqueous hydrochloric acid is heated to reflux for a period of 12 hours. The reaction mixture is then allowed to cool to room temperature, concentrated under reduced pressure, and co-evaporated four times with 25 ml of water. The crude material is dissolved in water, washed with ether and the aqueous layer is treated with activated charcoal. The solution is filtered hot, the filtrate is concentrated under reduced pressure, the residue dissolved in 20 ml of ethanol and treated with 1 ml of propylene oxide. The mixture is stirred until the precipitated solid is free of halogen. The solid is then filtered and recrystallised from methanol/acetone give P-[3-amino-2(S)-hydroxy-propyl]-P-methyl-phosphinic acid, m.p. 221°–222.5°, $^{31}$P-NMR spectrum: $\delta$=+38.9 ppm (D$_2$O), $[\alpha]_D^{25}$=–6.0° (c=0.887% in H$_2$O).

The starting material may be prepared as follows:

To a solution of 4.55 g of isobutyl O-trimethylsilyl-P-methyl-phosphonite in 100 ml of dry tetrahydrofuran are added 5.0 g of (2R)-glycidyl tosylate followed by 0.2 g of dry zinc chloride. The mixture is heated to reflux for a period of 3 hours under an inert gas atmosphere. The mixture is allowed to cool to room temperature, the solvent is evaporated under reduced pressure, the residue dissolved in 50 ml of chloroform, and this is stirred vigorously with 25 ml of water for a period of 0.5 hours. The organic layer is separated, dried over magnesium sulphate and the solvent is removed under reduced pressure. The residue is chromatographed on silica gel using 5 parts of ethyl acetate and 1 part of ethanol as eluent. There is obtained isobutyl P-[2(S)-hydroxy-3-tosyloxy-propyl]-P-methyl-phosphinate as a viscous oil, $^3$P-NMR spectrum: $\delta$=+54.5 and +53.4 ppm (CDCl$_3$), $[\alpha]_D^{25}$=+6.5 (c=0.54% in ethanol).

A solution of 3.32 g of isobutyl P-[2(S)-hydroxy-3-tosyloxy-propyl]-P-methyl-phosphinate and 1.19 g of sodium azide in 25 ml of dry dimethylformamide is heated to a temperature of 120° for a period of 3 hours, under an inert gas atmosphere. The reaction mixture is allowed to cool to room temperature, poured onto 50 ml of water and extracted twice with 100 ml of ethyl acetate. The organic extract is dried over magnesium sulphate and the solvent removed under reduced pressure. The residue is chromatographed on silica gel using 5 parts of ethyl acetate to 1 part of ethanol as eluent. There is obtained isobutyl P-[3-azido-2(S)-hydroxy-propyl]-P-methyl-phosphinate as a viscous oil, $^{31}$P-NMR spectrum: $\delta$=+54.8 and +53.7 ppm (CDCl$_3$), $[\alpha]_D^{25}$=+18.6 (0.56% in ethanol).

To a solution of 1.2 g of isobutyl P-[3-azido-2(S)-hydroxy-propyl]-P-methyl-phosphinate in 25 ml of ethanol are added 0.25 g of 5% palladium on charcoal. The resulting mixture is hydrogenated at 1 bar until hydrogen uptake ceases. The mixture is then filtered and the filtrate evaporated to give isobutyl P-[3-amino-2(S)-hydroxy-propyl]-P-(methyl)-phosphinate as a viscous oil, $^{31}$P-NMR spectrum: $\delta$=+55.6 and +54.6 ppm (CDCl$_3$), $[\alpha]_D^{25}$=+10.9 (c=0.50% in ethanol).

EXAMPLE 5

A solution of 1.6 g of isobutyl P-[3-amino-2(R)-hydroxy-propyl]-P-methyl-phosphinate in 20 ml of 36% aqueous hydrochloric acid is heated to reflux for a period of 12 hours. The reaction mixture is then allowed to cool to room temperature, concentrated under reduced pressure, and co-evaporated four times with 25 ml of water. The crude material is dissolved in water, washed with ether and the aqueous layer is treated with activated charcoal. The solution is filtered hot, the filtrate is concentrated under reduced pressure, the residue dissolved in 20 ml of ethanol and treated with 1 ml of propylene oxide. The mixture is stirred until the precipitated solid is free of halogen. The solid is then recrystallised from methanol/acetone to give P-[3-amino-2(R)-hydroxy-propyl]-P-methyl-phosphinic acid, m.p. 222°–225°, $^{31}$P-NMR spectrum: $\delta$=+38.8 ppm (D$_2$O), $[\alpha]_D^{25}$=+5.9 (c=0.918% in H$_2$O).

The starting material may be prepared as follows:

To a solution of 4.55 g of isobutyl O-trimethylsilyl-P-methyl-phosphonite in 100 ml of dry tetrahydrofuran are added 5.0 g of (2S)-glycidyl tosylate followed by 0.2 g of dry zinc chloride. The mixture is heated to reflux for a period of 3 hours under an inert gas atmosphere. The mixture is allowed to cool to room temperature, the solvent is evaporated under reduced pressure, the residue dissolved in 50 ml of chloroform, and this is stirred vigorously with 25 ml of water for a period of 0.5 hours. The organic layer is separated, dried over magnesium sulphate and the solvent is removed under reduced pressure. The residue is chromatographed on silica gel using 5 parts of ethyl acetate and 1 part of ethanol as eluent. There is obtained isobutyl P-[2(R)-hydroxy-3-tosyloxy-propyl]-P-methyl-phosphinate as a viscous oil, $^{31}$P-NMR spectrum: $\delta$=54.5 and +53.4 ppm (CDCl$_3$), $[\alpha]_D^{25}$=–6.8 (c=0.44% in ethanol).

A solution of 4.3 g of isobutyl P-[2(R)-hydroxy-3-tosyloxy-propyl]-P-methyl-phosphinate and 1.5 g of sodium azide in 25 ml of dry dimethylformamide is heated to a temperature of 120° for a period of 3 hours under an inert gas atmosphere. The reaction mixture is allowed to cool to room temperature, poured onto 50 ml of water and extracted twice with 100 ml of ethyl acetate. The organic extract is dried over magnesium sulphate and the solvent removed under reduced pressure. The residue is chromatographed on silica gel using 5 parts of ethyl acetate to 1 part of ethanol as eluent. There is obtained isobutyl P-[3-azido-2(R)-hydroxy-propyl]-P-methyl-phosphinate as a viscous oil, $^{31}$P-NMR spectrum: $\delta$=+54.8 and +53.7 ppm (CDCl$_3$), $[\alpha]_D^{25}$=–15.8 (0.51% in ethanol).

To a solution of 2.2 g of isobutyl P-[3-azido-2(R)-hydroxy-propyl]-P-methyl-phosphinate in 25 ml of ethanol is added 0.25 g of 5% palladium on charcoal. The resulting mixture is hydrogenated at 1 bar until hydrogen uptake ceases. The mixture is then filtered and the filtrate evaporated to give isobutyl P-[3-amino-2(R)-hydroxy-propyl]-P-methyl-phosphinate as a viscous oil, $^{31}$P-NMR spectrum: $\delta$=+55.6 and +54.6 ppm (CDCl$_3$), $[\alpha]_D^{25}$=–9.9 (0.66% in ethanol).

EXAMPLE 6

A solution of 0.5 g of isobutyl P-(3-tert.-butoxycarbonylamino-2-oxo-propyl)-P-methyl-phosphinate in 10 ml of 36% aqueous hydrochloric acid is heated to reflux for a period of 4 hours. The mixture is then allowed to cool to room temperature, concentrated under reduced pressure, and coevaporated twice with 20 ml of water. The crude product is dissolved in 20 ml of ethanol, 1 ml of propylene oxide is added, and the mixture is stirred until the precipitated solid is free of halogen. The solid is filtered and dried to give P-(3-amino-2-oxo-propyl)-P-methyl-phosphinic acid, m.p. 148°–149°, $^{31}$P-NMR spectrum: δ=32.8 ppm (D$_2$O).

The starting material may be prepared as follows:

To a solution of 6.1 g of diisopropylamine in 25 ml of dry tetrahydrofuran at 0° under an atmosphere of nitrogen are added 37.5 ml of a 1.6M solution of n-butyllithium in hexane. This solution is stirred for a period of 10 minutes and then cooled to −78°. To this is added, via a syringe, a solution of 9.0 g of isobutyl P,P-dimethyl-phosphinate in 50 ml of dry tetrahydrofuran and the mixture is stirred at −78° for a period of 1 hour. To this is then added a solution of 1.9 g of methyl N-tert.-butoxycarbonylaminoglycinate in 25 ml of dry tetrahydrofuran and the reaction mixture is allowed to warm to room temperature and is stirred for a period of 1 hour. 3 ml of glacial acetic acid are then introduced, followed by 50 ml of saturated sodium bicarbonate solution, and the aqueous layer is extracted twice with 100 ml of ether. The organic extract is dried over magnesium sulphate and concentrated under reduced pressure. The residue is chromatographed on silica gel using ethyl acetate as eluent. There is obtained isobutyl P-(3-t-butoxycarbonylamino-2-oxo-propyl)-P-(methyl)-phosphinate, m.p. 65°–68°, $^{31}$P-NMR spectrum: δ=+44.9 ppm (CDCl$_3$).

EXAMPLE 7

A solution of 4.0 g of ethyl P-(3-benzyloxycarbonylamino-1-hydroxy-propyl)-P-methyl-phosphinate in 50 ml of 5.0M aqueous hydrochloric acid is heated to reflux for 20 hours under an inert gas atmosphere. Then, the reaction mixture is cooled to room temperature and washed twice with 100ml each of dichloromethane and once with diethyl ether. The aqueous layer is evaporated to dryness at 50° under reduced pressure. The oily residue is then co-evaporated 5 times with 50 ml each of water and of absolute ethanol. The remaining white solid is dried under reduced pressure at 80° and then re-crystallised to afford P-(3-amino-1-hydroxy-propyl)-P-methyl-phosphinic acid hydrochloride of m.p. 115°–116.5°. This can be converted into the free compound by dissolving in ethanol and treating with propylene oxide yielding, after filtration and drying, P-(3-amino- 1-hydroxy-propyl)-P-methyl-phosphinic acid of m.p. 125°–126.5°.

The starting material may be prepared as follows:

A mixture of 5.18 g of 3-(benzyloxycarbonylamino)propionaldehyde, 2.7 g of ethyl P-methylphosphinate and 2,53 g of triethylamine is heated to 100° under an inert gas atmosphere for 2 hours. After cooling to room temperature the volatile materials are removed under reduced pressure to afford a viscous oil. Chromatography thereof on silica gel gives ethyl P-(3-benzyloxycarbonylamino-1-hydroxy-propyl)-P-methyl-phosphinate as a colourless, viscous oil.

EXAMPLE 8

A mixture of 520 mg (2.6 mmol) of ethyl P-(3-aminopropyl)-P-difluoro-methyl-phosphinate and 5 ml of 12M hydrochloric acid is refluxed for 3 hours and then evaporated to dryness. The residue is dissolved in 5 ml of methanol. To the stirred solution 25 ml of epoxypropane are added dropwise, upon which spontaneous crystallisation occurs. The crystals are collected and dried yielding P-(3-aminopropyl)-P-difluoro-methyl-phosphinic acid of m.p. 261°.

The starting material can be prepared as follows:

To a suspension of 15.8 g of sodium hydride in 500 ml of dry tetrahydrofuran 67 g (300 mmol) of ethyl P-(1,1-diethoxyethyl)phosphinate are added dropwise at such a rate that the reaction temperature does not exceed 25°. The reaction mixture is stirred for 1 hour at room temperature and cooled to −10°. Then 77.8 g (900 mmol) of chlorodifluoromethane are added. Stirring is continued for additional 2 hours, upon which 100 ml of ice-cold water are added. The reaction mixture is extracted 3-times with 500 ml each of dichloromethane. The extracts are combined, dried over magnesium sulphate, filtrated and evaporated to dryness yielding ethyl P-(2,2-diethoxyethyl)-P-difluoromethyl-phosphinate as a viscous oil of R$_f$=0.44 (dichloromethane/ethyl acetate; 9:1).

A mixture of 5 ml of dry ethanol and 10.9 ml (86.5 mmol) of trimethylchlorosilane is added to a solution of 15 g (57.6 mmol) of ethyl P-(2,2-diethoxyethyl)-P-difluoromethyl-phosphinate in 95 ml of dry dichloromethane. The reaction mixture is stirred for 3 hours at room temperature and then evaporated to dryness yielding ethyl P-difluoromethyl-phosphinate of R$_f$=0.1 (ethyl acetate).

660 mg (28.8 mmol) of sodium are dissolved in 40 ml of ethanol. The solution is cooled to −10° and 8.6 g (57.6 mmol) of ethyl P-difluoromethylphosphinate and 3.8 ml (57.6 mmol) of acetonitrile are added with stirring. The reaction mixture is then allowed to warm up to room temperature and stirred for additional 17 hours and then adjusted to pH 6 by addition of glacial acetic acid. The solvents are evaporated and the residue is dissolved in dichloromethane, washed twice with water, dried over magnesium sulphate and evaporated to dryness. The crude product is purified by chromatography on silica gel with ethyl acetate/dichloromethane (7:3) as eluent. The fractions containing the desired product are combined and evaporated to dryness yielding ethyl P-(2-cyanoethyl)-P-difluoromethyl-phosphinate as an oil of R$_f$=0.54 (above eluent).

A solution of 1.0 g (5.1 mmol) of ethyl P-(2-cyanoethyl)-P-difluoromethyl-phosphinate in 10 ml of dry ethanol is treated with 4 g of liquid ammonia and 0.3 g of Raney nickel. The reaction mixture is hydrogenated at 50° for 9 hours at 100 mbar. The reaction mixture is cooled, filtrated and evaporated to dryness. Chromatographic purification yields ethyl P-(3-aminopropyl)-P-difluoromethyl-phosphinate as a colourless oil of R$_f$=0.22 (dichloromethane/methanol/aqueous ammonia; 80:19:1).

EXAMPLE 9

A mixture of 4,53 g (30 mmol) of P-(5-aminopent-3-yl)phosphonous acid and 24.21 g (150 mmol) of hexamethyldisilazane is refluxed under argon while stirring for 16 hours. To the resulting solution 15 ml of diethylene glycol dimethyl ether are added and boiling is continued for additional 2 hours. The reaction mixture is cooled to 100° and 19.38 g (150 mmol) of N-ethyl-N,N-diisopropyl-amine are added over a period of 20 minutes. After cooling to 25°, 21.29 g (15 mmol) of methyliodide are added over a period of 20 minutes, the reaction temperature being kept at 25° with external cooling. The reaction mixture is stirred for 4 days, then cooled to 10°. The white precipitate is filtered off. The filtrate is evaporated under reduced pressure, and the residue diluted with 100 ml of cold dichloromethane and extracted three times with 50 ml each of 2N hydrochloric acid. The extracts are combined, evaporated to dryness and co-evaporated 2 additional times with 50 ml each of water to give a colourless oil. This oil is dissolved in 50 ml of methanol, 300 ml of propylene oxide are added and the mixture is kept at 4° overnight and then evaporated under reduced pressure. The crude product is purified by chromatography on 150 g of Opti-Up® $C_{12}$ with water as eluent. The fractions containing the desired product are combined and evaporated under reduced pressure. The solid residue is dried under reduced pressure yielding P-(5-aminopent-3-yl)-P-methyl-phosphinic acid×0.52 $H_2O$ (hygroscopic).

The starting material can be prepared in the following manner:

2.90 g (0.126 mol) of sodium are dissolved in 72 ml of ethanol. At from 0° to +5° 58.6 g (0.3 mol) of ethyl P-(diethoxymethyl)phosphonite and 42.3 ml (0.3 mol) of pent-2-enenitrile, dissolved in 72 ml of ethanol, are added while stirring over a period of 6 hours. The mixture is then allowed to warm to room temperature and stirring is continued for 16 hours. 7 ml of glacial acetic acid are added at 10°. Then, the solvent is removed under reduced pressure. The residue is dissolved in ethyl acetate, washed twice with water and dried over sodium sulphate. Evaporation in vacuo yields the cruder product as a yellow oil. After distillation at 100°/0.01 Torr ethyl P-(4-cyano(but-3-yl)-P-(diethoxymethyl)-phosphinate is obtained as a colourless oil.

73.4 g (0.264 mol) of ethyl P-(4-cyanobut-3-yl)-P-(diethoxymethyl)-phosphinate in 770 ml of dry ethanol are treated with 126 g of an 8% solution of ammonia in ethanol. Subsequently, 15 g of Raney-nickel and the resulting mixture is hydrogenated at 45° under atmospheric pressure. The catalyst is then filtered of and the filtrate is concentrated under reduced pressure. The crude product is distilled in vacuo to yield the ethyl P-(5-amino-pent- 3-yl)-P-(diethoxymethyl)-phosphinate (b.p.: 100°/0.01 Torr).

A solution of 61.88 g (0.22 mol) of ethyl P-(5-aminopent-3-yl)-P-(diethoxymethyl)-phosphinate in 220 ml of 36% aqueous hydrochloric acid is heated to reflux for a period of 6 hours. The reaction mixture is then allowed to cool to room temperature, concentrated under reduced pressure, and co-evaporated three times with 10 ml-portions of water. The crude material is dissolved in 100 ml of methanol, and 500 ml of propylene oxide are added while stirring. The mixture is left to stand overnight at 4° and the white precipitate is then filtered off and recrystallized from methanol/acetone to give pure hygroscopic P-(5-aminopent-3-yl)phosphorous acid [m.p.: 130°–140° (decomposition)].

EXAMPLE 10

To a mixture of 825 mg of diisopropylaminomethyl-polystyrene in 5 ml of acetonitrile are added 69.4 mg (0.2 mmol) of ethyl P-(4-amino-1,1,1-trifluoro-but-2-yl)-P-methyl-phosphinate trifluoroacetate while stirring at 25°. To this mixture are added 0.09 ml (0.7 mmol) of trimethylsilyl bromide. After stirring for 1 hour at 25°, the mixture is filtered and 299.78 mg (2 mmol) of sodium iodide and 217.28 mg (2 mmol) of trimethylsilyl chloride are added to the filtrate which is then stirred for 16 hours at 25°. The sodium chloride precipitated is filtered off and the filtrate is evaporated under reduced pressure to dryness. The crude product is dissolved in 2 ml of acetonitrile. 15 mg (0.83 mmol) of water are added to the resulting solution. After stirring for 1 hour at 25°, the solution is evaporated under reduced pressure to dryness and chromatographed on 50 g of Opti-Up® $C_{12}$ with acetonitrile as eluent to remove a small amount of the starting material. After re-eluting with water, the product-containing fractions are combined and evaporated under reduced pressure to give P-(4-amino-1,1,1-trifluoro-but-2-yl)-P-methyl-phosphinic acid hydroiodide as an oil; $^1$H-NMR spectrum: δ=3.20 ppm (m, 2H), 2.67 ppm (m, 1H), 2.15 (m, 2H), 1.42 ppm (d, 3H).

The starting material can be obtained, for example, as follows:

A solution of 2.16 g (20 mmol) of O-ethyl-P-methyl-phosphonous acid and 4.05 g (40 mmol) of triethylamine in 100 ml of dry tetrahydrofuran is stirred under an atmosphere of argon at 25°. To this solution are added at 25° 4.35 g (40 mmol) of trimethylsilyl chloride over a period of 10 minutes. A white precipitate is formed. The reaction mixture is stirred at 25° for additional 16 hours. Then, 2.42 g (20 mmol) of 4,4,4-trifluorocrotononitrile, dissolved in 20 ml of dry tetrahydrofuran, are added at 25° over a period of 10 minutes. The reaction mixture is refluxed for 40 hours, cooled to 25°, poured into ice-water and extracted with dichloromethane. The extracts are combined, washed with water, dried over anhydrous sodium sulphate and evaporated under reduced pressure to dryness. The crude product is chromatographed on 200 g of silica gel with trichloromethane as eluent. The product-containing fractions are combined and evaporated to give ethyl P-(3-cyano-1,1,1-trifluoro-prop-2-yl)-P-methyl-phosphinate as an oil.

250 mg of platinum oxide are added to a solution of 458.28 mg (2 mmol) of ethyl P-(3-cyano-1,1,1-trifluoro-prop-2-yl)-P-methyl-phosphinate dissolved in 28 ml of trifluoroacetic acid, and the resulting mixture is hydrogenated at 25° and 4 bar. The catalyst is filtered off and the filtrate is evaporated to dryness under reduced pressure. The resulting crude product is chromatographed on 70 g of Opti-Up® $C_{12}$ with acetonitrile as the eluent. The product-containing fractions are combined and evaporated under reduced pressure to give ethyl P-(4-amino-1,1,1-trifluoro-but-2-yl)-P-methyl-phosphinate trifluoroacetate as an oil.

EXAMPLE 11

The hydrogenation of P-(3-aminopropen-1-yl)-P-methyl-phosphinic acid carried out by conventional hydrogenation techniques well known in the an yields P-(3-aminopropyl)-P-methyl-phosphinic acid, identical with the product obtained in Example 1.

The starting material can be prepared, for example, as follows:

A solution of 2.7 g of diisobutyl P,P-(dimethyl)-methylenebisphosphinate in 25 ml of dry tetrahydrofuran is added to a suspension of 0.23 g of sodium hydride in 10 ml of dry tetrahydrofuran under an inert gas atmosphere. The mixture is stirred at room temperature under an inert gas atmosphere until the gas evolution ceases. The mixture is then added to a solution of 1.8 g of N-(formylmethyl)-phthalimide in 25 ml of dry tetrahydrofuran at 0° under an inert gas atmosphere. The reaction mixture is allowed to warm to room temperature and then stirred for one hour. 5 ml of saturated ammonium chloride solution are added. The mixture is extracted twice with 25 ml-portions of diethyl ether. The combined organic extracts are dried over magnesium sulphate. The solvent is removed under reduced pressure and the resulting residue purified by chromatography on silica gel using 5 parts of ethyl acetate to 1 part of ethanol as eluent. The fractions containing product are combined and concentrated under reduced pressure to give isobutyl P-(3-phthalimidopropen-1-yl)-P-methyl-phosphinate as a viscous oil [$^{31}$P-NMR spectrum: δ=+34.1 ppm (CDCl$_3$)].

A solution of 0.72 g of isobutyl P-(3-phthalimidopropen-1-yl)-P-methyl-phosphinate in 25 ml of aqueous hydrochloric acid (36%) is heated to reflux for 15 hours. The reaction mixture is then allowed to cool to room temperature. Some insoluble material is removed by filtration and the filtrate is concentrated under reduced pressure. The resulting crude material is co-evaporated four times with 25 ml-portions of water, dissolved in 25 ml of ethanol and treated with 1–2 ml of propylene oxide. The precipitated solid is removed by filtration and purified by chromatography on Dowex 50W X2 resin with water as eluent. The fractions containing the desired product are combined and evaporated and the resulting solid is dried to give P-(3-aminopropen-1-yl)-P-methyl-phosphinic acid of m.p. 209°–213° [$^{31}$P-NMR spectrum: δ=+30.4 ppm (D$_2$O)].

EXAMPLE 12

In an analogous manner as described in any one of Examples 1 to 11, also the following compounds can be manufactured:

P-(3-aminopropyl)-P-fluoromethyl-phosphinic acid and
P-(3-aminopropyl)-P-trifluoromethyl-phosphinic acid.

EXAMPLE 13

Tablets, each containing 75 mg of the active ingredient, for example, P-(3-amino-2-oxo-propyl)-P-methyl-phosphinic acid, can be manufactured in the following manner:

| Constituents (for 1000 tablets) | |
|---|---|
| active ingredient | 75.0 g |
| lactose | 268.5 g |
| corn starch | 22.5 g |
| polyethylene glycol 6000 | 5.0 g |
| talcum | 15.0 g |
| magnesium stearate | 4.0 g |
| demineralised water | q.s. |

Preparation: The solid ingredients are first forced through a sieve of 0.6 mm mesh width. Then, the active ingredient, lactose, talcum, magnesium stearate and half of the starch are homogeneously mixed. The other half of the starch is suspended in 65 ml of water, and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed into tablets of approximately 10 mm diameter which are concave on both sides and have a breaking notch on the upper side.

EXAMPLE 14

Tablets, each containing 10 mg of the active ingredient, for example, P-(3-amino- 2-oxo-propyl)-P-(methyl)-phosphinic acid, can be prepared in the following manner:

| Constituents (for 1000 tablets) | |
|---|---|
| active ingredient | 10.0 g |
| lactose | 25.0 g |
| corn starch | 308.5 g |
| polyethylene glycol 6000 | 32.5 g |
| talcum | 10.0 g |
| magnesium stearate | 15.0 g |
| demineralised water | q.s. |

Preparation: The solid ingredients are first forced through a sieve of 0.6 mm mesh width. Then, the active ingredient, lactose, talcum, magnesium stearate and half of the starch are homogeneously mixed. The other half of the starch is suspended in 65 ml of water, and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed into tablets of approximately 10 mm diameter which are concave on both sides and have a breaking notch on the upper side.

EXAMPLE 15

Gelatine dry-filled capsules, each containing 150 mg of the active ingredient, for example, P-(3-amino-2-oxo-propyl)-P-methyl-phosphinic acid, can be prepared in the following manner:

| Constituents (for 1000 capsules) | |
|---|---|
| active ingredient | 150.0 g |
| microcrystalline cellulose | 30.0 g |
| sodium laury sulphate | 2.0 g |
| magnesium stearate | 8.0 g |

The sodium lauryl sulphate is added to the active ingredient (lyophilised) through a sieve of mesh width 0.2 mm and these two components are intimately mixed for 10 minutes. The microcrystalline cellulose is then added through a sieve of mesh width 0.9 mm and the mixture is again intimately mixed for 10 minutes. Finally, the magnesium stearate is added through a sieve of mesh width 0.8 mm and, after mixing for additional 3 minutes, the mixture is introduced into size 0 (elongated) gelatine dry-filled capsules in portions of 390 mm.

EXAMPLE 16

A 0.2% injection or infusion solution of the active ingredient, for example, of P-(3-amino-2-oxo-propyl)-P-methyl-phosphinic acid, can be prepared in the following manner:

| Constituents (for 2500 ml) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and then water is added to give a volume of 2500 ml. For the preparation of dosis unit forms, portions of 1.0 or 2.5 ml are introduced into glass ampoules (each containing 2.0 or 5.0 mg of the active ingredient, respectively).

We claim:

1. A P-substituted aminoalkylphosphinic acid of the formula

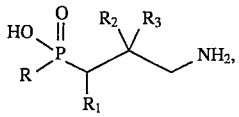

wherein R denotes an optionally fluorinated methyl group, $R_1$ denotes hydrogen, lower alkyl, lower alkoxy, hydroxy, halogen or a fluorinated methyl group and $R_2$ and $R_3$ denote hydrogen or $R_2$ denotes hydroxy, lower alkoxy or halogen and $R_3$ is hydrogen or $R_2$ and $R_3$ together represent an oxo group, with the exception of P-(3-amino-2-oxo-propyl)-P-methyl-phosphinic acid and racemic P-(3-amino-2-hydroxy-propyl)-P-methyl-phosphinic acid, or a salt thereof with the exception of alkali metal salts and the ammonium salt of P-(3-aminopropyl)-P-methyl-phosphinic acid.

2. A compound according to claim 1, wherein R denotes methyl, fluoromethyl, difluoromethyl or trifluoromethyl, $R_1$ denotes hydrogen, lower alkyl, lower alkoxy, hydroxy, halogen, fluoromethyl, difluoromethyl or trifluoromethyl and $R_2$ and $R_3$ denote hydrogen or $R_2$ denotes hydroxy, lower alkoxy or halogen and $R_3$ denotes hydrogen or $R_2$ and $R_3$ together represent oxo, with the exception of P-(3-amino-2-oxo-propyl)-P-methyl-phosphinic acid and racemic P-(3-amino-2-hydroxy-propyl)-P-methyl-phosphinic acid, or a salt thereof with the exception of alkali metal salts and the ammonium salt of P-(3-aminopropyl)-P-methyl-phosphinic acid.

3. A compound according to claim 1, of the formula I, wherein R denotes methyl, fluoromethyl, difluoromethyl or trifluoromethyl, $R_1$ denotes hydrogen or $C_1$–$C_4$alkyl, $R_2$ denotes hydrogen or hydroxy and $R_3$ denotes hydrogen or $R_2$ and $R_3$ together represent oxo, with the exception of P-(3-amino-2-oxo-propyl)-P-methyl-phosphinic acid and racemic P-(3-amino-2-hydroxy-propyl)-P-methyl-phosphinic acid, or a salt thereof with the exception of alkali metal salts and the ammonium salt of P-(3-aminopropyl)-P-methyl-phosphinic acid.

4. A compound according to claim 1, wherein R denotes methyl, $R_1$ is hydrogen, and wherein $R_2$ represents hydrogen or hydroxy and $R_3$ is hydrogen or $R_2$ and $R_3$ together represent oxo, with the exception of P-(3-amino-2-oxo-propyl)-P-methyl-phosphinic acid provided that, when $R_2$ denotes hydroxy, the C-atom it is attached to has S-configuration, in the free form or in the form of an acid addition salt.

5. A compound of the formula I, wherein R denotes methyl, fluoromethyl, difluoromethyl or trifluoromethyl, $R_1$ denotes hydroxy and $R_2$ and $R_3$ are hydrogen, or a salt thereof.

6. A compound as claimed in claim 1 being P-(3-aminopropyl)-P-methyl-phosphinic acid in the free form.

7. A compound as claimed in claim 1 being P-[3-amino-2(R)-hydroxy-propyl]-P-methyl-phosphinic acid or an acid addition or base salt thereof.

8. A compound as claimed in claim 1 being P-[3-amino-2(S)-hydroxy-propyl]-P-methyl-phosphinic acid or an acid addition or base salt thereof.

9. A compound as claimed in claim 1 being P-(1-aminopent-3-yl)-P-methyl-phosphinic acid or an acid addition or base salt thereof.

10. A compound as claimed in claim 1 being P-(4-amino-1,1,1-trifluoro-but-2-yl)-P-methyl-phosphinic acid or an acid addition or base salt thereof.

11. A compound as claimed in claim 1 being P-(3-aminopropyl)-P-fluoromethyl-phosphinic acid or an acid addition or base salt thereof.

12. A compound as claimed in claim 1 being P-(3-aminopropyl)-P-difluoromethyl-phosphinic acid or an acid addition or base salt thereof.

13. A compound as claimed in claim 1 being P-(3-aminopropyl)-P-trifluoromethyl-phosphinic acid or an acid addition or base salt thereof.

14. A compound as claimed in claim 1 being an acid addition or base salt of P-(3-amino-2-oxo-propyl)-P-methyl-phosphinic acid.

15. A compound as claimed in claim 1 being P-(4-aminobut-2-yl)-P-methyl-phosphinic acid or an acid addition or base salt thereof.

16. A compound as claimed in claim 1 being P-(3-amino-1-hydroxy-propyl)-P-methyl-phosphinic acid or an acid addition or base salt thereof.

17. A pharmaceutical composition containing a compound according to claim 1 in admixture to conventional pharmaceutical carriers.

* * * * *